United States Patent [19]
Bridges

[11] Patent Number: 5,976,078
[45] Date of Patent: Nov. 2, 1999

[54] APPARATUS AND METHOD FOR HOLDING INTESTINES OUT OF AN OPERATIVE FIELD

[75] Inventor: Doye R. Bridges, Victoria, Tex.

[73] Assignee: BioEnterics Corporation, Carpintera, Calif.

[21] Appl. No.: 09/132,211

[22] Filed: Aug. 17, 1998

Related U.S. Application Data

[62] Division of application No. 08/763,287, Dec. 11, 1996, Pat. No. 5,795,290, which is a division of application No. 08/405,529, Mar. 16, 1995, Pat. No. 5,651,762, which is a continuation-in-part of application No. 08/089,713, Jul. 9, 1993, abandoned.

[51] Int. Cl.⁶ .................................................. A61B 17/00
[52] U.S. Cl. ........................ 600/207; 600/206; 600/208; 600/235
[58] Field of Search ..................................... 600/201, 206, 600/207, 208, 210, 235, 203; 128/898

[56] References Cited

U.S. PATENT DOCUMENTS

| | | | |
|---|---|---|---|
| 1,213,005 | 1/1917 | Pillsbuury | 606/121 X |
| 1,480,680 | 1/1924 | Glover . | |
| 1,550,403 | 8/1925 | Turkus . | |
| 1,944,009 | 1/1934 | Homer . | |
| 2,305,289 | 12/1942 | Coburg | 128/132 |
| 2,938,519 | 5/1960 | Marco | 128/285 |
| 3,288,131 | 11/1966 | Garland . | |
| 3,364,919 | 1/1968 | Hinnicutt . | |
| 3,863,639 | 2/1975 | Kleaveland | 128/303 R |
| 3,882,855 | 5/1975 | Schulte et al. . | |
| 4,048,987 | 9/1977 | Hurson . | |
| 4,291,687 | 9/1981 | Sinnreich | 128/129 |
| 4,533,356 | 8/1985 | Bengmark et al. | 604/358 |
| 4,637,377 | 1/1987 | Loop . | |
| 4,777,943 | 10/1988 | Chvapil | 128/850 |
| 4,850,953 | 7/1989 | Haber et al. | 600/32 |
| 4,889,107 | 12/1989 | Kaufman . | |
| 4,981,465 | 1/1991 | Ballan et al. | 600/32 |
| 5,346,484 | 9/1994 | Van Lindert . | |
| 5,460,621 | 10/1995 | Gertzman et al. . | |
| 5,520,609 | 5/1996 | Moll et al. | 600/207 X |
| 5,651,762 | 7/1997 | Bridges | 600/208 X |
| 5,795,290 | 8/1998 | Bridges | 600/208 X |

FOREIGN PATENT DOCUMENTS

| | | | |
|---|---|---|---|
| 536850 | 4/1993 | European Pat. Off. . | |
| 2416687 | 10/1979 | France | 606/191 |
| 797668 | 1/1981 | U.S.S.R. . | |

OTHER PUBLICATIONS

Disposable Laparotomy sponge and packaging by Kendell Healthcare Products Company, The Kendell Company of Mansfield, Massachusetts © 1990 Kendall.

Brookwalter™ Retractor System distributed by Codman and Shurtleff, Inc. of Randolph, Massachusetts. (no date) (one page).

O'Sullivan–O/Connor self–retaining abdominal retractor distributed by Codman and Shurtleff, Inc. of Randloph, Mssachusetts. (one page) (no date).

(List continued on next page.)

*Primary Examiner*—Jeffrey A. Smith
*Attorney, Agent, or Firm*—Akin, Gump, Strauss, Hauer & Feld, LLP

[57] ABSTRACT

A nonabsorbent holding member adapted for use within an abdominal cavity of a patient defined by an anterior wall, a posterior wall and two lateral walls to keep the patient's bowels out of the operative field during open pelvic surgery. The holding member has a peripheral edge formed of a resiliently deformable material sized to be received within the abdominal cavity. The resilient deformation of at least a portion of the peripheral edge of the holding member results in a residual reactive force against the abdominal cavity to assist in positioning the holding member in the abdominal cavity.

20 Claims, 4 Drawing Sheets

OTHER PUBLICATIONS

Stedman's Medical Dictionary 25th Edition Illustrated, Copyright © 1990, Williams & Wilkins, three cover sheets and pp. 1242–1244 (six pages total).

Poron® S2000 Silicone Data Sheet, Poron®S2000 Silicone Preliminary Product Properties, published by Rogers Corporation of Woodstock, Connecticut (no date) (1 page total).

USP Class VI testing of S2000–80–08250 sponsored by Rogers Corporation of Woodstock Connecticut (no date) (1 page total).

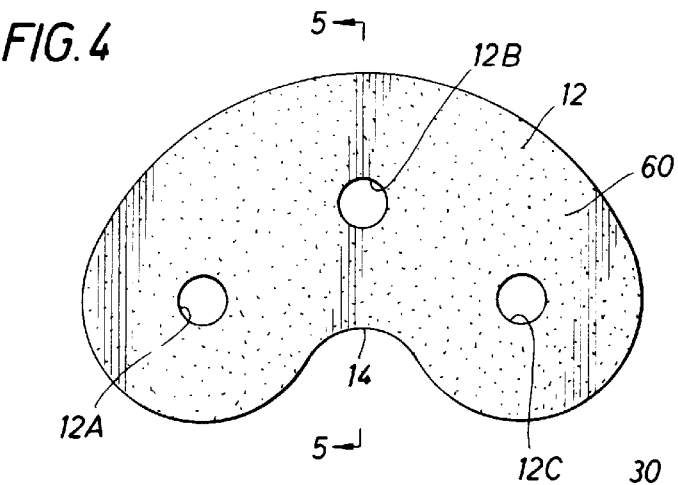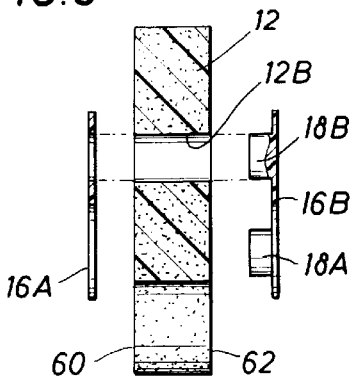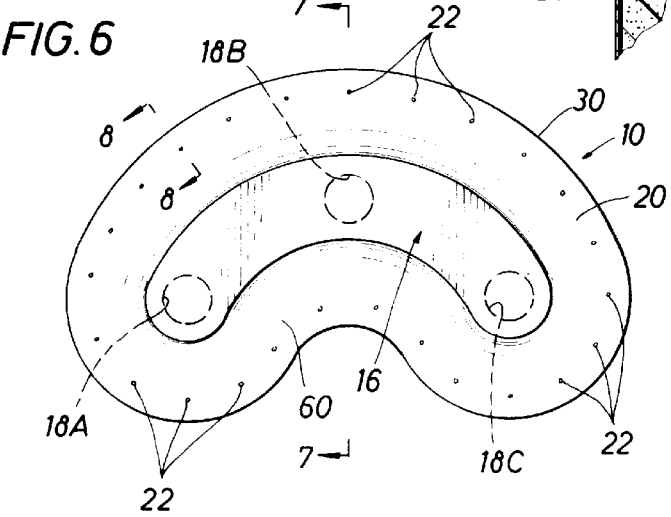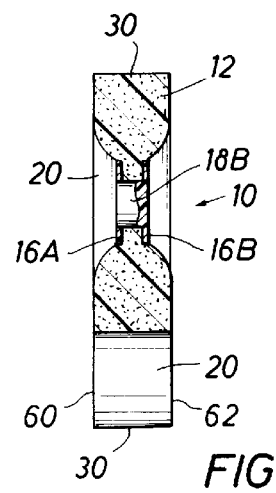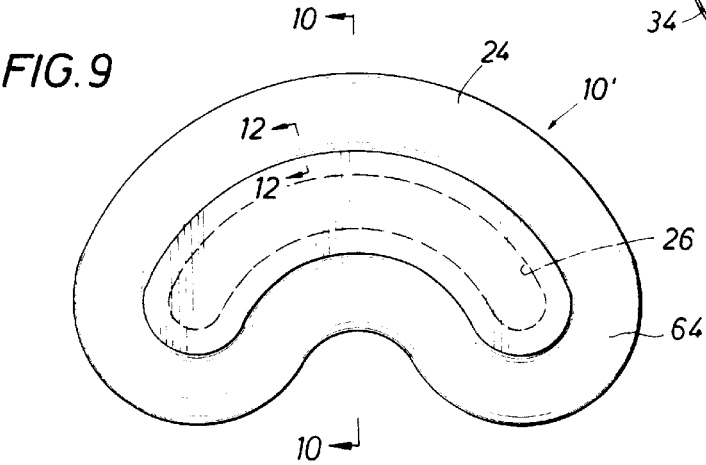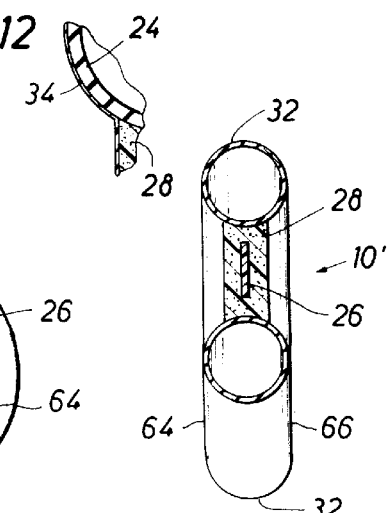

APPARATUS AND METHOD FOR HOLDING INTESTINES OUT OF AN OPERATIVE FIELD

This is a divisional application of Ser. No. 08/763,287 filed Dec. 11, 1996, now U.S. Pat. No. 5,795,290, which is a divisional application of Ser. No. 08/405,529 filed on Mar. 16, 1995, now U.S. Pat. No. 5,651,762, which is a continuation-in-part of application Ser. No. 08/089,713 filed Jul. 9, 1993, now abandoned.

FIELD OF THE INVENTION

The invention relates to an apparatus for holding intestines out of an operative field. In particular, the invention relates to a nonabsorbent bean-shaped surgical holding member sized to be received in a patient's abdominal cavity to hold the omentum and intestines out of the operative field during open transabdominal pelvic surgery. An operating procedure for using the holding member is also disclosed.

BACKGROUND OF THE INVENTION

When pelvic surgery is performed trans-vaginally or with a laparoscope there is generally no delay in return of normal motility to the intestines. However, when open pelvic surgery is required, intra-operative bowel (e.g. intestine and omentum) irritation can result.

Peristalsis is successive waves of involuntary contractions passing along the walls of the intestine forcing the contents onward. The absence or reduction of peristalsis following surgery is referred to as post-operative ileus. Ileus results in bloating, cramping, nausea and vomiting as a result of the mechanical and functional obstruction of the intestines during post-operative recovery. This usually increases a hospital stay by twenty-four to forty-eight hours.

Additionally, during open pelvic surgery the surgeon must be careful while holding the intestines out of the operative field so as not to constrict, or worse, cut off proper flow of the patient's vena cava and aorta that provides blood to and from the heart.

The use of devices for retaining and preventing movement of the viscera, or organs, adjoining the field of an abdominal surgical procedure is common surgical practice. Such retaining devices include pads, such as towels or large sponges, such as a 4 ply-18"×18" disposable laparotomy sponges supplied by Kendell Healthcare Products Company, the Kendell Company, of Mansfield, Mass. These loose woven cloth sponges are used to pack the omentum and the intestines into the abdominal cavity and are often held in place by a metal retractor blade of sufficient width and depth, such as used with the Weinstein retractor device, the "BOOK-WALTER" retractor system, or the O'Sullivan-O'Connor self-retaining abdominal retractor. Both the "BOOK-WALTER" and O'Sullivan-O'Connor retractors are distributed by Codman and Shurtleff, Inc. of Randolph, Mass. The O'Sullivan-O'Connor retractor includes two fixed blades, two removable small blades and one large removable blade.

U.S. Pat. Nos. 4,533,356 and 5,346,484 propose surgical devices for internal use during surgical abdominal operations. However, these two surgical devices, like the pads, are designed to absorb blood and/or wound fluid. It is the inventor's present belief that a nonabsorbent, as compared to an absorbent, holding member reduces irritation and the resultant post-operative ileus.

A disposable abdominal retracting pad known by the trade name DISARP is disclosed in U.S. Pat. No. 4,889,107. This retractor is stated to comprise a flexible flat metal rod having no memory enclosed in urethane plastic foam in turn wrapped in an absorbent woven nylon.

U.S. Pat. No. 4,889,107 further discloses an abdominal retractor that comprises a barrier member forming a surgical dam for retaining viscera in an abdominal cavity during surgery which is stated to be nonabsorbent and is capable of being bent to a selected configuration. A core member made from a soft, malleable aluminum or, alternatively, a metal capable of returning to a predetermined shape after being heated to a certain temperature ("Nitinol") is enclosed within the barrier member to retain the barrier member in a selected configuration. A flexible material such as a plastic foam or silicone rubber encloses the core member and both are covered by a material impermeable to the passage of blood such as silicone rubber, polyvinylchloride or latex.

While U.S. Pat. No. 4,889,107 discloses in FIG. 4 that the side walls and end walls of the barrier member are upright when positioned adjacent to a surgical field in an abdominal cavity, there is no teaching of a fixed presized indentation in the barrier member to provide proper flow through the patient's aorta and vena cava to and from the heart. A fixed presized indentation would relieve the surgeon from physically having to bend the member to a proper configuration. Also, it is believed that the barrier member of U.S. Pat. No. 4,889,107 could bend out of the desired configuration either before or during its use, placing a life threatening constriction on the patient's aorta or vena cava. Further, an indentation in the barrier member of U.S. Pat. No. 4,889,107 was not discussed, disclosed or deemed necessary since the barrier member was not contemplated to be positioned within the walls of the abdominal cavity but, as shown in FIG. 4, the rectangular-shaped barrier member is only placed adjacent to a surgical field with the top and end walls free.

A presized nonabsorbent holding member with a presized or preshaped indentation to allow proper flow of the patient's aorta and vena cava would be desirable. Additionally, an operation procedure whereby the nonabsorbent holding member having a slippery surface that blocks the bowels is positioned between the anterior, lateral and posterior walls of the abdominal cavity would reduce irritation of the bowels and the resultant postoperative discomfort of ileus and shorten the hospital stay while providing a more positive means for holding the bowels out of the operative field during open pelvic surgery.

SUMMARY OF THE INVENTION

A nonabsorbent holding member having a slippery surface adapted for use within a patient's abdominal cavity defined by an anterior wall, a posterior wall and two lateral walls to keep the omentum and intestines out of the operative field during open pelvic surgery is provided. A holding member having a peripheral edge formed of a resiliently deformable foam is presized to be received within the abdominal cavity. The resilient deformation of at least a portion of the peripheral edge of the holding member results in a residual reactive force against the abdominal cavity walls. This residual reactive force assists in positioning of the holding member in the abdominal cavity. Alternatively, the holding member can have a cross section equal or greater than the abdominal cavity to substantially block the intestines in the upper abdomen from the operative field. This blocking or holding of the intestines is achieved while a presized indentation in the holding member allows proper fluid flow to and from the heart via the patient's aorta and vena cava. The plastic foam in the holding member is advantageously compressed adjacent a core formed of a material having a memory to increase the density of the foam adjacent the core to protect the aorta and vena cava. The material used for the holding member including the core has a memory when it has a capacity for returning to a former condition or shape independent of external forces, such as, but not limited to, unfolding, uncoiling, unrolling, unbending by the user.

Additionally, a procedure for using the nonabsorbent holding member to assist in holding a portion of the intestines within the abdominal cavity defined by the anterior wall, posterior wall and two lateral walls during the open pelvic operation is provided.

BRIEF DESCRIPTION OF THE DRAWINGS

The object, advantages and features of the invention will become more apparent by reference to the drawings which are appended hereto and wherein like letters or numerals indicate like parts and wherein an illustrative embodiment of the invention is shown, of which:

FIG. 4 is a resiliently deformable plastic foam portion of an alternative embodiment of the holding member of the present invention;

FIG. 5 is a section taken along lines 5—5 of FIG. 4 additionally illustrating the alignment of the side plates of the core before assembly;

FIG. 6 is a view similar to FIG. 4 with the side plates assembled and a cover or coating provided over the alternative embodiment of the holding member of the present invention;

FIG. 7 is a section view taken along lines 7—7 of FIG. 6;

FIG. 8 is an enlarged section view taken along lines 8—8 of FIG. 6 better illustrating the cover or coating for the holding member of the present invention;

FIG. 9 is another alternative embodiment of the present invention comprising an inflatable tube;

FIG. 10 is a section view taken along lines 10—10 of FIG. 9;

FIG. 12 is an enlarged section view taken along lines 12—12 of FIG. 9 better illustrating the cover or coating for the alternative embodiment of the holding member of the present invention;

DETAILED DESCRIPTION OF PREFERRED EMBODIMENT

Figure 2:
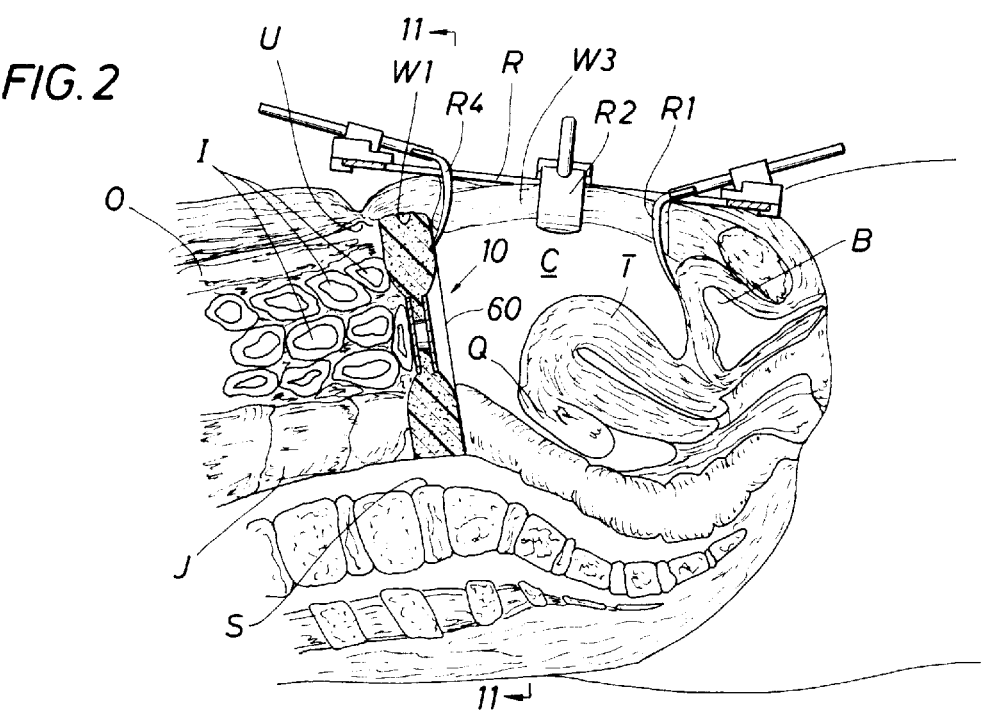
FIG. 2 is an enlarged cross section elevational view of the patient's abdominal cavity with a holding member inserted between the anterior wall adjacent the umbilicus and the posterior wall around a patient's vena cava and aorta.
Figure 11:
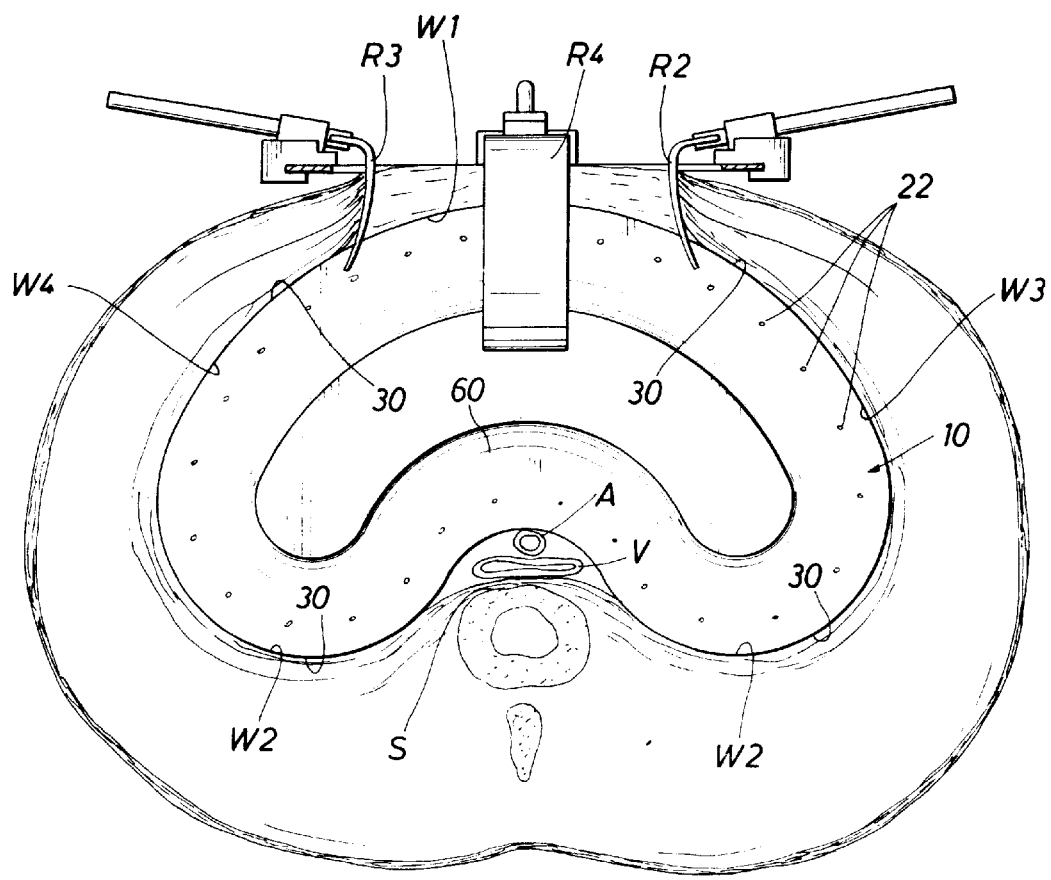
FIG. 11 is an enlarged section view taken along lines 11—11 of FIG. 2 better illustrating the positioning of a holding member of the present invention between the abdominal cavity walls.
Figure 15:
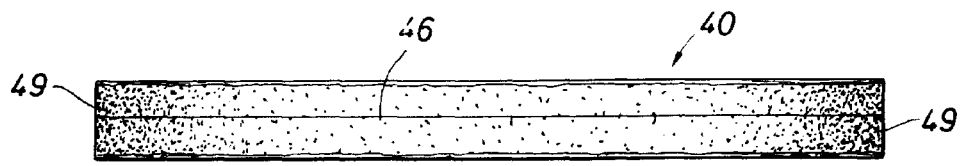
FIG. 15 is a bottom view of the holding member of FIG. 14.
Figure 13:
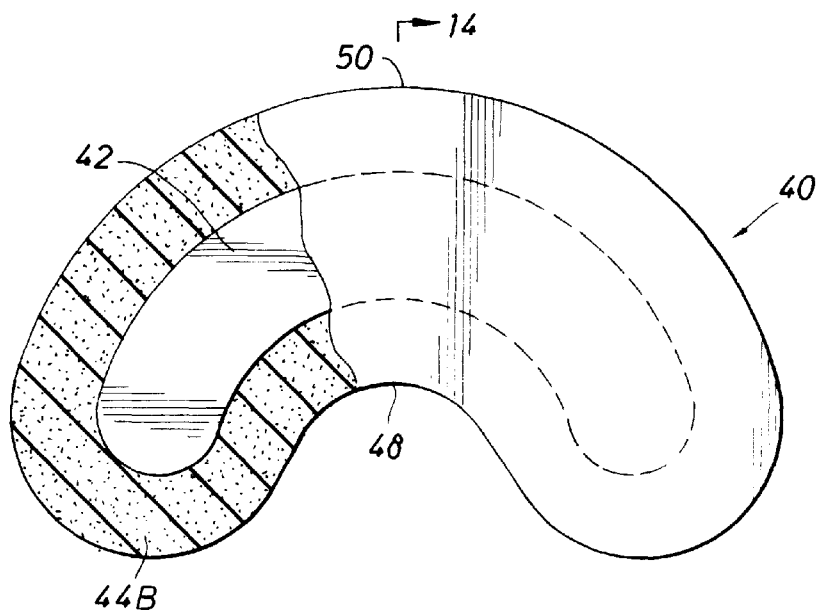
FIG. 13 is the preferred embodiment of the present invention with aportion of the holding member foam and its nonabsorbent cover or coating cut away to better illustrate the core, the remaining portion of the core in the holding member shown in phantom view.
Figure 14:
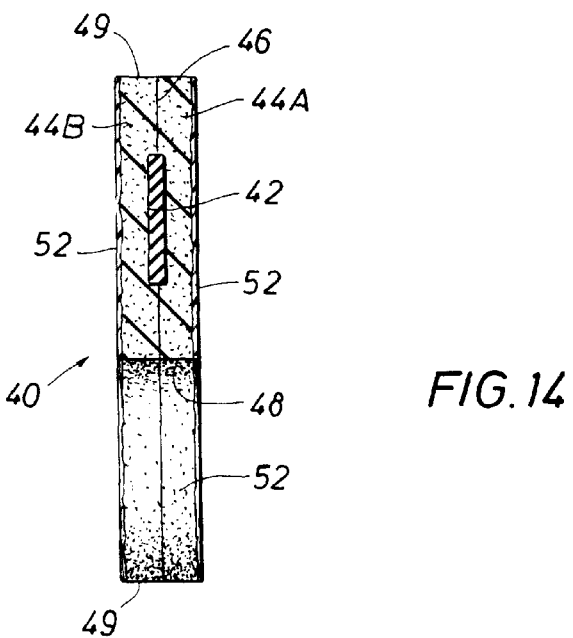
FIG. 14 is a section view taken along lines 14—14 of FIG. 13.

The preferred embodiment of the holding member, generally indicated at 40 in FIGS. 13, 14 and 15, is sized to be received within the abdominal cavity C of a patient P defined by an anterior wall $W_1$, a posterior wall $W_2$, lateral wall $W_3$ and lateral wall $W_4$, as generally shown in FIGS. 2 and 11. The holding member 40 is preferably constructed of a coated plastic foam completely embedding a more rigid core, as will be described below in detail. In alternative embodiments, as shown in FIGS. 2 and 4 to 11, holding members, generally indicated as 10 and 10', are fabricated from a coated plastic foam and a core, or a coated inflatable tube having a foam embedded core, respectively, as will be described below in detail.

Turning first to FIG. 5, in one alternative embodiment the holding member 10 includes a resiliently deformable plastic foam member 12 having an upper or front surface 60, a lower or rear surface 62, and three bores 12A, 12B and 12C therein. Though three bores are shown in the member 10, a different number of bores could be used. The plastic foam member 12 is bean-shaped having an overall curved configuration including an indentation 14. A preferred medium sized holding member 10 would include the center height from the top of the indentation 14 to the top of the foam member 12 through the axis of bore 12B of approximately 10 centimeters. The overall length of the holding member 10 along the bottom of bores 12A and 12C and the tangent of indentation 14 is approximately 26.0 centimeters. Preferably, the bores are approximately 2.0 centimeters in diameter. The overall height of the holding member 10 is approximately 16.0 centimeters with a total uniform thickness of approximately 2.7 centimeters. This 16.0 centimeter overall height and 10.0 centimeter actual holding member height provides a 6.0 centimeter clearance from the top of indentation 14 to the bottom of the holding member about the patient's aorta and vena cava. The width of each side plate 16A and 16B of the core 16 is 4.5 centimeters. The plastic foam member 12 is preferably cut from a cellular silicone foam available from Rogers Corporation of Woodstock, Conn. under the trademark "PORON" S2000 silicone though could be fabricated from other comparable medical grade polymers or materials. Other possible materials that could be used for the holding member could include those disclosed in U.S. Pat. Nos. 2,938,519; 3,863,639; 4,637,377; 4,777,943; 4,889,107 and 4,981,465, which are incorporated by references herein for all purposes.

Though not shown, the holding member 10' of FIGS. 9 and 10 could have a rigid core, such as two cores like core 26, relocated on opposed outside surfaces, such as the front surface 64 and rear surface 66 of the holding member to provide a more positive engagement surface between the retractor blade $R_4$ and the holding member 10'. Additionally, a positive attachment means could be provided between the retractor blade $R_4$ and the core of any of the disclosed holding members; such as a keyhole in the core and a corresponding key member on the retractor blade $R_4$.

Returning to FIG. 5, the side plates 16A and 16B are preferably molded from a fairly stiff elastomer, such as a liquid that is injection molded and heat and pressure vulcanized to provide a gum-type material with a memory. Such liquid has been previously supplied as No. 7-6860 by Dow Corning of Midland, Mich. or is now available as Part No.

PS1771 by Applied Silicone Corporation of Ventura, Calif. The three cylindrical connecting members 18A, 18B and 18C are preferably 1 centimeter in length. Upon assembly of side plate 16A with side plate 16B, the foam member 12, which is preferably 2.7 centimeters thick in its uncompressed state, is compressed to 1 centimeter. This approximately 3 to 1 compression of the foam will increase the density of the foam adjacent the central core or side plates 16A and 16B to further protect the patient's aorta A and vena cava V during insertion and use of the holding member. Any suitable adhesive for assembly of connecting members 18A, 18B and 18C to side plates 16A and 16B may be used or common mechanical locking devices for connecting the core 16 together may be used. A preferred adhesive is No. 586 NuSil Medical Grade Adhesive - 1137 by NuSil Silicone Technologies of Carpinteria, Calif.

After the side plates have been assembled, the entire holding member 10 preferably is coated with a polymer layer or coating 20, such as a dimethyl silicone elastomer, as best shown in FIG. 8. The slippery resultant surface on the front surface 60 and the rear surface 62 of holding member from this elastomer coating further reduces tissue reaction by allowing the bowels to contact and move relative to the holding member without significant friction. This layer 20, as discussed further below, must be soft, compliant, pliable, resiliently deformable and nonporous so that it permits compression of the foam member 12 while being nonabsorbent. This layer 20 may be applied by dipping or spraying onto the foam member 12. Preferably, the holding member is dipcoated by dipping in the coating material for approximately 5 minutes and allowed to air dry for approximately 1 hour then re-dipped for another 5 minutes and again allowed to air dry for approximately another 1 hour. The holding member is then placed into an oven and cured at 300° F. for approximately 3 hours. A preferred coating is Part No. 40,000 medical grade dimethyl silicone elastomer by Applied Silicone Corporation of Ventura, Calif. dispersed in Syxlene.

After the holding member 10 is completely coated, the layer 20 covering the front surface 60 of the holding member 10 could, if desired, be perforated with a plurality of holes 22 to allow air to vent with compression and expansion of the holding member. The holding members, as shown in the Figures, would be wrapped, packaged and terminally sterilized by gas or gamma radiation. As can be seen, a simple manufacture process could be used to reduce the cost of the holding member.

As best shown in FIGS. 9 and 10, an alternative embodiment of the holding member 10' having an upper or front surface 64 and a lower or rear surface 66, is constructed of an air filled tube 24 generally having the same overall U-shaped or bean-shaped configuration and dimensions as holding member 10. Though the holding member 10' is shown constructed of one continuous tube, the tube could comprise a plurality of chambers (not shown) strategically placed to prevent inadvertent deflation during an operation. The central core 26 of the member 10' preferably is fabricated from a vulcanized silicone elastomer having a memory, as described above, embedded in a foam 28, such as the "PORON" cellular silicone foam, as described above. The foam 28 is in turn attached to tube 24 by a conventional heating process or an adhesive, such as the above-described NuSil-1137 adhesive. As best shown in FIG. 12, the holding member 10' is preferably dipcoated, as described above, by a soft, flexible, pliable, nonporous and nonabsorbent material 34, such as Applied Part No. 40,000 medical grade dimethyl silicone elastomer or other suitable material similar to the preferred coating.

Turning now to FIGS. 13–15, the preferred holding member 40 having an upper or front surface 68, and a lower or rear surface 70 is shown. The preferred holding member includes a core 42, as best shown in FIGS. 13 and 14, preferably made of a vulcanized silicone elastomer previously available from Dow Corning and now available from Applied Silicone Corporation, as described above. This core is centrally embedded in a cellular silicone foam such as the "PORON" S2000 silicone by Rogers Corporation of Woodstock, Conn. The "PORON" S2000 silicon is a closed cell foam that is nonabsorbent to blood and other body fluids. The foam is cut and provided in two sections 44A, 44B, such as shown in FIG. 14. The vulcanized silicone elastomer core 42 is centrally attached to one of the sections with use of an adhesive, such as the NuSil 1137 adhesive. Preferably, at least 3 centimeters of cellular silicone foam are provided at all points between the peripheral edge of the holding member 40 and the core 42. The other section of the foam is then positioned by the use of adhesive preferably along the full engaging surface 46, including the other side of the core, to provide a unitary one piece holding member. The holding member should then be allowed to cure for 24 hours, trimmed of excess adhesive and cleaned with isopropyl alcohol.

In the preferred embodiment, once the two sections of the foam 44A and 44B are joined by the adhesive with the core therein, the holding member 40 may then be completely dip coated, as described above, with a nonabsorbent layer 52, as best shown in FIG. 14. Preferably, the coating is Part No. 40,000 a medical grade dimethyl silicone elastomer by Applied Silicone Corporation of Ventura, Calif. While the holding member would be nonabsorbent without the coating because of the use of a closed cell foam, the coating is preferred to insure the nonabsorbency and to provide the preferred slippery surface of the holding member 40. While the front surface 68 and the rear surface 70 of the foam cut from the sheet will have a smooth surface, the edge will have a rougher surface because of the foam cells. Upon coating, the front surface 68 and the rear surface 70 will become more slippery and the edge will still have a sufficiently rough surface to provide good engagement with the abdominal cavity walls.

A preferred medium size holding member 40 would include a center height from the top of the indentation 48 to the top of the holding member 40 at 50 of approximately 10.0 centimeters. The overall length of the holding member 40 at the tangential intersection at 48 is approximately 26.0 centimeters. The overall height of the holding member 40 is approximately 16.0 centimeters with a thickness of approximately 2.7 centimeters. This 16.0 centimeter overall height and 10.0 centimeter actual holding member height provides 6.0 centimeters between the indentation to the bottom of the holding member about the patient's aorta and vena cava.

While both of the alternative embodiments, holding member 10, as shown in FIGS. 4–8, and holding member 10', shown in FIGS. 9 and 10, have the same general bean-shaped configuration of the preferred holding member 40, the holding members 10 and 40 have squared off peripheral edges 30 and 49, respectively, and the holding member 10' has a radiused or curved peripheral edge 32. However, it is to be understood that the holding members 10 and 40 could be fabricated with a radiused, curved, combination radiused and flat peripheral edge or other geometric combination edge.

Procedure for Use

Turning now to FIGS. 1–3 and 11, the procedure for use of the holding member is shown. During open pelvic surgery, a number of different presized holding members in individual sterile packages will preferably be available to the surgeon. For example, aged patients and smaller patients would use a different sized holding member than that described above for a medium sized patient. However, the overall configurations of these different size holding members can be predetermined by averaging a number of Computerized Axial Tomography (CAT) scan cross sections on the abdominal cavity.

Figure 3:
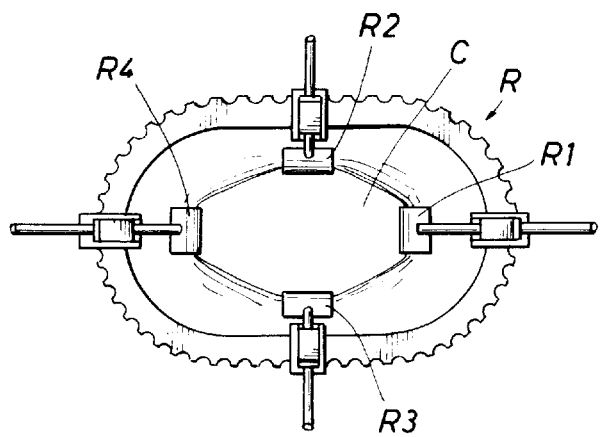
FIG. 3 is a top view of a conventional four-way retractor positioned on the patient as shown in FIGS. 1 and 2.

As best shown in FIGS. 2 and 3, an incision is used to open the pelvic area of the patient P. A lower midline incision, lower transverse incision or any other medically acceptable opening may be used. After retracting the lateral abdominal walls $W_3$ and $W_4$ with blades $R_2$ and $R_3$, respectively, using a conventional 4-way retractor, such as the "BOOKWALTER" retractor R, as shown in FIGS. 1–3 and 11, the urinary bladder B is retracted with a suitably sized lower retractor blade $R_1$. The vertical distance between the sacral spine S and the umbilicus U or anterior wall $W_1$ adjacent the umbilicus U is then measured. This measurement is used to select the proper size holding member.

Figure 1:
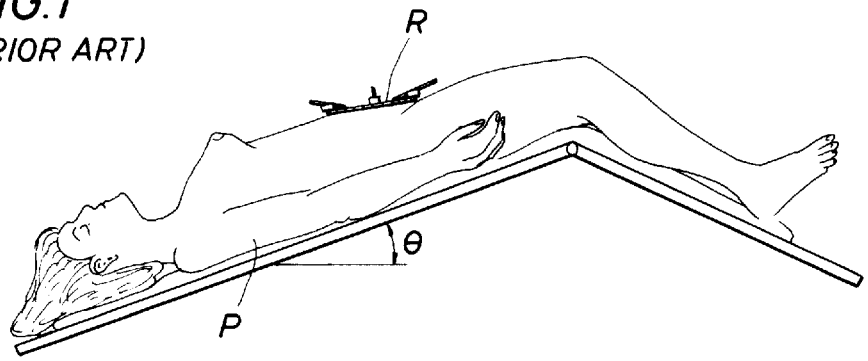
FIG. 1 is an elevational view of the positioning of a conventional retractor on a patient positioned in the "Trendelenburg" position before a holding member of the present invention is inserted in the abdominal cavity.

Prior to insertion of the holding member, the patient P is placed momentarily into an extreme "Trendelenburg" position allowing the intestines I and omentum O along with the colon J to recede into the upper abdomen as much as possible. FIG. 1 illustrates the basic "Trendelenburg" position, though the angle θ could be larger as desired by the surgeon. The holding member is then moved through the incision into the abdominal cavity C. If desired, using the concave portion of the holding members 10, 10' as a scoop or the front surface 68 of the holding member 40, the intestines I are moved further upwards in the upper abdomen until the member is positioned at or preferably 2 centimeters below the umbilicus U. The rear surface of the holding members 10 and 10', as best shown in FIG. 2, are concave to centrally locate the intestines. As best shown in FIG. 11, the front surface of the holding member could include a plurality of holes to allow air to vent to and from the holding member, if desired. Even though the holding member is vented, it would still be nonabsorbent if a nonabsorbent material is used for the holding member, such as a closed cell foam.

The holding members 10 and 40 will preferably have a cross section of an additional 2 centimeters of foam in all directions than the actual average relaxed abdominal cavity measurements, except, of course, at the respective indentations 14, 48. This additional material will allow for compression and variations of cavity contours and sizes.

The anterior and lateral abdominal walls of an average patient can withstand considerable pressure from the inside or tension loading during surgery. However, as best shown in FIG. 11, the patient's aorta A and vena cava V above the spine S in the center of the posterior wall $W_2$ should be protected from more than about 15 millimeters mercury pressure. Since the cores 16, 42 of the respective holding members 10, 40 are constructed of a more rigid elastomer, such as the vulcanized silicone elastomer described above, the holding member will transmit pressure to all the abdominal walls W. This core however should not come into contact with the aorta A and vena cava V. Of course, the density of the foam increases as the foam is compressed to the core. In the holding member 10 as the foam is compressed, a denser foam is adjacent the exposed core to protect the aorta A and vena cava V. In holding members 10', 40, the more rigid core 26, 42 is embedded in a soft foam 28, 44A, 44B to act as a buffer between the more rigid core 26, 42 and the resilient and compliant outer plastic tube 24 or the resilient and compliant 30 foam 44A, 44B.

After the holding member has been inserted, which should only take 1 or 2 minutes, the patient P is repositioned to a more supine or horizontal position to reduce pressure on the patient's diaphragm. As a precaution, it is recommended that the patient's pulse be checked in the common iliac arteries after insertion of the holding member and one finger inserted between the patient's aorta and vena cava and the holding member to be sure that pressure on the vena cava is not enough to obstruct flow. As a backup, if there is a reduction in venus return, the anesthetist would observe significant tachycardia.

In the alternative, the holding members as shown in the Figures can be sized so that minimal or no pressure is exerted on the abdominal walls with the holding member acting merely as a blocking member used in combination with the abdominal cavity walls to keep the intestines out of the operative field.

The fourth or upper blade $R_4$ of the retractor R is then moved into the incision and positioned adjacent the core of the respective holding member to hold the intestines I and omentum O in the upper abdomen clear of the operative field on the uterus T and/or ovary Q.

After completing the intra-abdominal phase of the surgery, the holding member is removed along with the 4-way retractor and the incision is closed in the usual manner.

A The foregoing disclosure and description of the invention are illustrative and explanatory thereof, and various changes in the size, shape and materials, as well in the details of the illustrated construction may be made without departing from the spirit of the invention.

I claim:

1. Apparatus adapted for use within an abdominal cavity of a patient, said cavity defined by an anterior wall, a posterior wall and lateral walls, said apparatus comprising: a holding member adapted to be received in the abdominal cavity and having an inflatable outer portion having an edge, said holding member including an indentation and a core formed of a polymer that is more rigid than said edge to resist folding of said holding member.

2. Apparatus of claim 1 wherein said core is embedded in a foam.

3. Apparatus of claim 2 wherein said core is fabricated from a vulcanized silicone elastomer.

4. Apparatus of claim 1 wherein said inflatable outer portion is a plastic tube.

5. Apparatus adapted for use within an abdominal cavity of a patient, said cavity defined by an anterior wall, a posterior wall and lateral walls having intestines therein, said apparatus comprising
  a holding member sized to be received within the abdominal cavity and having an inflatable outer portion including an edge, said holding member having an indentation and a core formed of a polymer that is more rigid than said edge to resist folding of said holding member, said edge of said holding member being configured so that positioning of the holding member between the cavity walls substantially blocks the intestines in the abdominal cavity.

6. Apparatus of claim 5 wherein said core is embedded in foam.

7. Apparatus of claim 6 wherein said core is fabricated from a material that is more rigid than said foam.

8. Apparatus of claim 6 wherein said core is centrally positioned in said holding member.

9. Apparatus of claim 5 wherein said edge of said holding member is sized to extend beyond the cross-section of the relaxed patient's abdominal cavity to enhance said residual reactive force.

10. Apparatus of claim 5 wherein said holding member is substantially bean-shaped.

11. Apparatus of claim 5 wherein said indentation is adapted to be positioned about the patient's aorta and vena cava.

12. Apparatus of claim 5 further comprising a nonabsorbent coating for said holding member to resist absorption of fluids.

13. Apparatus of claim 12 wherein said coating is a silicone elastomer.

14. Method for retracting a portion of the intestines within the abdominal cavity of a patient defined by an anterior wall, a posterior wall and lateral walls during an operation, comprising the steps of opening the abdomen, and defoaming a portion of a peripheral edge of an inflatable portion of a holding member between the walls of the abdominal cavity, said holding member having a core formed of a polymer that is more rigid than said edge to resist folding of said holding member.

15. Method of claim 14 further comprising the step of positioning the patient's pelvis higher than the patient's shoulders to allow the intestines to recede in the upper abdomen before positioning the holding member in the abdominal cavity.

16. Method of claim 14 further comprising the step of positioning the patient in a supine position after the holding member is positioned in the abdominal cavity.

17. Method of claim 14 further comprising the step of retracting the holding member in the abdominal cavity with a retractor blade.

18. Method of claim 14 further comprising the step of measuring the distance between the sacral spine and the umbilicus of the patient, and selecting the proper size holding member for positioning in the abdominal cavity.

19. Method of claim 14 further comprising positioning the holding member approximately two centimeters below the umbilicus.

20. Method of claim 14 wherein the holding member applies a reactive force against the anterior and lateral abdominal walls of the abdominal cavity greater than fifteen millimeters mercury pressure.

* * * * *

UNITED STATES PATENT AND TRADEMARK OFFICE
CERTIFICATE OF CORRECTION

Patent No.: 5,976,078
Dated: November 2, 1999
Inventors: Doye R. Bridges

It is certified that errors appear in the above-identified patent and that said Letters Patent is hereby corrected as shown below:

On column 7, line 67, please replace "compliant 30 foam" with -- compliant foam --.
On column 8, line 26, please replace "A The" with -- The --.

In claim 14, line 6, please replace "defoaming" with -- deforming --.

Signed and Sealed this

Twenty-seventh Day of February, 2001

Attest:

NICHOLAS P. GODICI

Attesting Officer

Acting Director of the United States Patent and Trademark Office